United States Patent [19]

Kuhn

[11] Patent Number: 5,396,011
[45] Date of Patent: Mar. 7, 1995

[54] CATALYTIC ALKYLATION OF AROMATIC COMPOUNDS WITH ALKENES

[75] Inventor: Deborah K. Kuhn, Erie, Pa.

[73] Assignee: Mallinckrodt Chemical, Inc., Chesterfield, Mo.

[21] Appl. No.: 997,381

[22] Filed: Dec. 28, 1992

[51] Int. Cl.$^6$ .......................... C07C 2/64; C07C 2/68; C07D 307/02
[52] U.S. Cl. .................... 585/455; 585/446; 585/467; 568/700; 568/38; 568/687; 568/18; 568/25; 568/42; 568/77; 568/317; 568/628; 549/506
[58] Field of Search .............. 585/455, 467, 446; 568/700, 38, 687, 18, 25, 42, 77, 317, 628; 549/506

[56] References Cited

U.S. PATENT DOCUMENTS

| | | |
|---|---|---|
| 2,572,701 | 10/1951 | Corson et al. |
| 4,233,139 | 11/1980 | Murrell et al. |
| 4,673,767 | 6/1987 | Nimry et al. ................ 585/467 |
| 4,721,810 | 1/1988 | Hargis . |
| 5,113,034 | 5/1992 | Soled et al. ................ 585/510 |

FOREIGN PATENT DOCUMENTS

| | | |
|---|---|---|
| 61-183230 | 8/1986 | Japan . |
| 1288339 | 11/1989 | Japan . |

OTHER PUBLICATIONS

Kozorezov, Yu. I,; Chemical Abstracts, vol. 75, No. 23, p. 292.
Tanabe, Hattori, and Yamaguchi, Surface Properties of Solid Superacids, Critical Reviews in Surface Chemistry, vol. 1, Issue 1 (1990), pp. 1–25.
M., Hino and K. Arata, Synthesis of Solid Superacid of Tungsten Oxide Supported on Zirconia and its Catalytic Action for Reactions of Butane and Pentane, J. Chem. Soc., Chem. Commun., 1988, pp. 1259–1260.
Chemical Abstracts 111:164488b, Alkylation of Benzene on Superacid Catalyst (M. Yamamoto), Kenkyu Holoku-Tokyo-toritsu Kogyo Gijutsu Senta 1988, (18) 85–8).
Chemical Abstracts 107:58245c, Alkylation of Phenol and Pyrocatechol by Isobutyl Alcohol Using Superacid Catalysts (R. A. Rajadhyaksha and D. D. Chaudhari, Ind. Eng. Chem. Res. 1987, 26(7), 1276–1280).

Primary Examiner—Helen M. S. Sneed
Assistant Examiner—E. D. Irzinski
Attorney, Agent, or Firm—Jeffrey S. Boone

[57] ABSTRACT

An aromatic compound (such as benzene) is alkylated with a alkene (such as propylene) by contacting the two compounds together in the presence of a tungsten on zirconia catalyst. The reaction preferably takes place at elevated temperature and elevated pressure. The process of the invention has very high selectivity and conversion, and produces no or only very low amounts of undesirable oligomers (as measured by bromine number).

22 Claims, No Drawings

CATALYTIC ALKYLATION OF AROMATIC COMPOUNDS WITH ALKENES

BACKGROUND OF THE INVENTION

This invention is concerned with the alkylation of aromatic compounds with alkenes. In particular it is concerned with the selection of catalysts to permit such reactions to proceed with a high degree of conversion and selectivity, i.e.: with a minimum formation of by-products such as polyalkylated species and alkene dimers and trimers.

The catalyst art is a notoriously unpredictable field. A catalyst that works well in one application may fail completely in a closely related application. Similarly, minor changes in a catalyst, such as using a slightly different support, may dramatically alter the catalyst's activity or selectivity. Further, one must not look only at a single characteristic of a catalyst. For a catalyst to be commercially viable, it must have excellent conversion and selectivity (i.e.: low byproduct formation), a reasonable lifetime, and physical properties allowing it to withstand the rigors of commercial operations.

The alkylation of aromatic compounds with alkenes is known. For instance, U.S. Pat. No. 2,572,701 (1951; B. Corson, et. al.; Koppers Company, Inc.) discloses the alkylation of benzene with propylene to produce cumene, using liquid sulfuric acid as a catalyst. The use of liquid catalysts has obvious process difficulties in a commercial manufacturing situation.

Current commercial processes for the production of cumene from benzene and propylene use a solid phosphoric acid catalyst ("SPA"). The SPA is generally clay or diatomaceous earth which has been saturated or impregnated with phosphoric acid, formed into extrudates or spheres, and calcined. To maintain the activity of the SPA it is necessary to add 100 to 200 ppm water to the feed stream. However, this water leads to phosphoric acid leaching off of the SPA catalyst, causing costly downstream equipment corrosion. Further, the amount of water reaching the catalyst bed must be tightly regulated, as too little will result in coking, while too much will destroy the physical integrity of the catalyst. In either case, the catalyst will be rendered inactive.

The use of solid acid catalysts for acid catalyzed reactions is also known. U.S. Pat. No. 4,721,810 (1988; D. Hargis; Ethyl Corporation) teaches the alkylation of aromatic amines with ethers, in the presence of a B-sub-group metal oxide alkylation catalyst, preferably a Group IV-B metal oxide (preferably a titanium oxide) with or without a minor proportion of a Group VI-B (preferably a molybdenum oxide) or Group VIII (preferably an iron oxide) metal oxide. This reference does not address the problem of alkylation with alkenes.

U.S. Pat. No. 4,233,139 (1980; L. Murrell, et. al.; Exxon Research & Engineering Co.) discloses the use of a catalyst selected from the group consisting of the oxides of tungsten, niobium, and mixtures thereof, and tungsten or niobium oxides in combination with one or more additional metal oxides selected from the group consisting of tantalum oxide, hafnium oxide, chromium oxide, titanium oxide, and zirconium oxide, supported on an inorganic refractory oxide support for catalytic cracking. The abstract of this patent contains the word "alkylation" but in view of the teachings in the patent of dealkylation, this may be an error. In any event, there is no enabling support for the use of these materials for alkylation processes.

Japanese patent publication JP 61 183,230 (World Patents Index Acc. No. 86-255378139, priority date 85.01.12, publication date 86.08.15; Keishitsu Ryubun Sh) teaches the manufacture of 2,2,3-trimethylpentane by reacting butene(s) with isobutene over a super acid catalyst. The catalyst is prepared by treating zirconium hydroxide or zirconium oxide with a sulphate-radical-containing solution and heating. The acid strength of the catalyst ($H_o$) is greater that $-10.6$. This reference does not address the alkylation of aromatic compounds. Moreover, the reaction it teaches is, in the instance of the alkylation of aromatic compounds with alkenes, a destructive side reaction. This reference would suggest that this class of catalyst not be used for alkylation with alkenes.

K. Arata and M. Hino, Synthesis of Solid Superacid of Tungsten Oxide Supported on Zirconia and its Catalytic Action, *Proc.—Int. Congr. Catal.*, 9th, Volume 4, 1727–1734, disclose a solid superacid catalyst with an acid strength of $Ho \leq -14.52$. The catalyst is obtained by impregnating $Zr(OH)_4$ or amorphous $ZrO_2$ with aqueous ammonium metatungstate and calcining. The catalyst was used for several reactions, including the acylation of aromatics with acetic and benzoic acids (specifically the acylation of toluene with benzoic anhydride). The catalyst is reported to be more stable than "sulfate-treated materials". The same authors report similar data in M. Hino and K. Arata, Synthesis of Solid Superacid of Tungsten Oxide Supported on Zirconia and its Catalytic Action for Reactions of Butane and Pentane, *J. Chem. Soc., Chem. Commun.*, 1988, p. 1259–1260. This reference does not address alkylation reactions.

Chemical Abstracts 111:164488b, Alkylation of Benzene on Superacid Catalyst (M. Yamamoto, *Kenkyu Holoku—Tokyotoritsu Kogyo Gijutsu Senta* 1988, (18), 85-8) reports that the alkylation of benzene with methanol, n-hexene, n-decene, or ethyl ether with various superacid catalysts was carried out in a fixed bed type apparatus with a continuous flow system at atmospheric pressure. In the alkylation of benzene with methanol, $Zr(OH)_4.H_2SO_4$ and $Ti(OH)_4.H_2SO_4$ were active at low temperature, but were unstable at high temperature. In the alkylation of benzene with n-hexene, the yield of cumene depended on the calcination temperature of $SbF_5.SiO_2.Al_2O_3$. The thermal cracking products of n-hexene were further cracked over superacid catalyst. In the alkylation of benzene with ethyl ether, ethyl benzene was produced at 80° C. and the activity of $NH_4F.HF.SiO_2.Al_2O_3$ was stable at 200° C.

Chemical Abstracts 107:58245c, Alkylation of Phenol and Pyrocatechol by Isobutyl Alcohol Using Superacid Catalysts (R. A. Rajadhyaksha and D. D. Chaudhari, *Ind. Eng. Chem. Res.* 1987, 26(7), 1276–80), teaches the use of perfluorinated sulfonic acid resin catalysts such as Nafion-H catalyst to alkylate phenol and pyrocatechol with isobutyl alcohol. The chosen catalysts were reported to be superior than equivalent loadings of 98% sulfuric acid.

Tanabe, Hattori, and Yamaguchi, Surface Properties of Solid Superacids, *Critical Reviews in Surface Chemistry*, Volume 1, Issue 1 (1990), pages 1–25, is a lengthy review article looking generally at solid superacid catalysts. It discloses the use of $WO_3/ZrO_2$ for the acylation of toluene with benzoic anhydride and the skeletal isomerization of butane and pentane. In a different section the article discloses the use of $SO_4^{2-}/TiO_2$—$ZrO_2$, $SO_4^{2-}/ZrO_2$, and $SO_4^{2-}/TiO_2$ for the alkylation of benzene with propylene. It was also noted that no activity was observed when these supports did not contain the $SO_4^{2-}$ functionality.

DETAILED DESCRIPTION OF THE INVENTION

In this specification and claims, numerical values and ranges are not critical unless otherwise stated. That is, the numerical values and ranges may be read as if they were prefaced with the word "about" or "substantially".

One component of the invention is a zirconia substrate or support. By "zirconia" is meant an oxide of zirconium. An exemplary zirconia is zirconium oxide ($ZrO_2$). Zirconium oxide is an article of commerce, but can be conveniently made by reacting a zirconium salt such as zirconium chloride, zirconium acetate, or zirconium nitrate ($ZrO(NO_3)_2 \cdot (H_2O)_x$) with a suitable base such as aqueous ammonium hydroxide ($NH_4OH$). The precipitate formed may be filtered, washed, and dried to obtain zirconium hydroxide ($Zr(OH)_4$). When calcined, the hydroxide will be converted to zirconium oxide. The zirconia may be in any form, such as orthorhombic or monoclinic.

Zirconium oxide alone is not effective as a catalyst in this invention. In order to be operable, it must be combined with (activated by) an acidic tungsten moiety. Because, as with most catalysts, the active sites must be finely divided and evenly distributed to be highly effective, it is most practical to apply the tungsten group to the zirconium hydroxide as a liquid (i.e.: by impregnation). However, other methods such as coprecipitation, wet mulling, and evaporation are well known in the art and may be used. The tungsten moiety may be added by dissolving ammonium meta tungstate in water and applying (e.g.: by spraying) the solution to the zirconia support.

After the tungsten moiety is mechanically added to the support, it is necessary to calcine the catalyst to render it effective. However, it will frequently be desirable to first granulate and/or shape the catalyst into a shape and size that will be convenient to handle. For the catalysts of this invention, tablets, extrudates, and spheres are particularly convenient physical forms. Desirably, after the tungsten is applied to the support, the catalyst will be dried with low heat. Large granules formed in the drying process may be broken up by milling or grinding. Then the catalyst will be tableted, preferably with the addition of a minor amount of a tableting aid such as a wax or other binder or lubricant. Finally, the catalyst will be calcined. Calcining generally takes place at 400° to 1000° C, desirably 600° to 1000° C., preferably 700° to 900° C.

The process of the invention requires that an aromatic compound and an alkene be contacted together in the presence of the above catalyst.

By "aromatic compound" is meant an aromatic hydrocarbon or substituted aromatic hydrocarbon (preferably a hydrocarbon), having a least one carbon atom on the aromatic ring available for alkylation. Suitable aromatic hydrocarbons include benzene, toluene, and xylene. Suitable substituted aromatic hydrocarbons include oxygenated species such as phenols, furan, cresols, resorcinol, phenyl ethers, phenones, and sulfur-containing analogs.

By "alkene" is meant a hydrocarbon having at least one (and preferably only one) olefinic bond, preferably in the form of an α-unsaturation. Such alkenes may be straight chained (preferred) or branched, so long as the branching does not sterically interfere with the alkylation reaction. Generally the alkenes will have 2 to 32, desirably 2 to 18, more desirably 2 to 16, preferably 3 to 10, more preferably 3 or 4, and most preferably 3 carbon atoms.

The process of the invention may be carried out in a variety of conditions, but desirably takes place in a commercial batch or continuous (preferred) reactor. In a continuous reactor the catalyst tablets will be loaded into a reaction column and the reactants passed through the column at elevated temperature and preferably elevated pressure. The temperature and pressure may vary depending on the precise nature of the reactants, catalyst, and desired product, but will generally fall within certain ranges. The temperature will generally be 25 to 500, preferably 100 to 300, and most preferably 150° to 250° C. The pressure (relative to atmospheric pressure) will generally be 50 to 7,000, preferably 300 to 5,000, and most preferably 2000 to 4000 kPa. The use of higher molecular weight materials will make the lower pressure ranges more feasible.

The quantity of catalyst used will depend on many variables such as the precise catalyst used, temperature, pressure, reactants, reactant feed rate, and yield vs. cost considerations.

The invention will be further explained in the following examples. In the examples, all parts and percentages are by weight unless otherwise specified.

EXAMPLE 1

Tungstate Zirconia Catalyst 1 kg of aqueous zirconium nitrate solution (20% zirconium oxide) was diluted to 2 liters with de-ionized water in a well agitated stainless steel vessel. Dilute ammonium hydroxide (29 weight % $NH_4OH$) was slowly added until the pH was between 7.2 to 7.4 at ambient temperature. The resulting gelatinous precipitate was aged for 30 minutes, maintaining the pH at 7.2 to 7.4 by adding additional $NH_4OH$ as necessary. The precipitate was filtered, washed with de-ionized water until the conductivity of the filtrate was 5 micromhos, dried in an oven at 120° C., and identified as zirconium hydroxide ($Zr(OH)_4$).

103.6 g of ammonium meta tungstate was dissolved in enough de-ionized water (about 250 ml) to fill the pore volume of 500 g of the dry zirconium hydroxide solids. The solution was sprayed onto the zirconia powder and the powder was then dried at 120° C. The dried powder was then granulated (or milled) to a uniform powder and formed into tablets after the addition of 3 weight percent of a lubricant/binder (Acrawax). The tablets were then calcined by slowly heating to 825° C. and maintaining that temperature for 4 hours. After calcining the support had changed from zirconium hydroxide to orthorhombic zirconium oxide ($ZrO_2$). The finished catalyst tablets had a calculated loading of 15 weight % tungsten. Similar tablets were made with 3.5% tungsten and 10% tungsten. Tablets were also made with 15% tungsten where the zirconium support was derived from zirconyl chloride.

EXAMPLE 2

Alkylation Reactions 25 cm$^3$ of the catalyst of Example 1 was packed into a single zone, fixed bed, jacketed reactor equipped with a 1/16 inch (1.6 mm) axial thermowell and inert material placed above and below the catalyst bed to aid feed diffusion. The reactor dimensions were 5/8 inches (15.9 mm) outside diameter and 30 inches (0.762 m) long. The bed aspect ratio (length/diameter) was 11.2. The feed composition was

| benzene | 90.51 weight % |
|---|---|
| propylene | 4.81 weight % |
| propane | 4.68 weight % |
| water | 100 ppm |

The feed stream was pumped into the reactor as 1.2 hour$^{-1}$ LHSV in upflow mode at a pressure of 450 psig (3.1 MPa). The temperature was varied (either 120° C., 175° C., or 230° C.) and conversion determined by GLC (gas-liquid chromatography). The results are reported in Table I.

The data show that the process of the invention has high activity, high selectivity, and results in a product with a very low bromine number (a high bromine number is an indication of undesirable alkene oligomer formation), and low polyalkylated species.

COMPARATIVE EXAMPLE A

Other Alkylations

The procedure of Example 2 was generally followed except that various other catalysts were used. The results are reported in Table I. In Table I, the following designations are used for the catalysts:

Unactivated Zirconia

Unactivated ZrO$_2$: zirconium oxide prepared as in Example I, but without any activating group Supported Phosphoric Acid Catalysts SPA-M: a supported phosphoric acid catalyst sold by Enichem as CA-131 alkylation catalyst SPA-U: a supported phosphoric acid catalyst sold by UOP as "UOP #1"

Zeolite Catalysts

LZY-82: a catalyst sold by Union Carbide as a 1/16" (1.6 mm) extrudate

H$^+$-Mordenite: a hydrogen form Mordenite 1/8" (3.2 mm) extrudate

H$^+$-Y: a hydrogen form Y zeolite 1/8" (3.2 mm) tablet

H$^+$-X: a hydrogen form X zeolite 1/8" (3.2 mm) tablet

H$^+$-L: a hydrogen form L zeolite 1/8" (3.2 mm) tablet

SP-115: a 1/16" (1.6 mm) silicalite extrudate sold by Union Carbide

Miscellaneous Catalysts

Sulfated ZrO$_2$: Similar to Example 1, but with 20 ml of 1N sulfuric acid per gram of zirconia instead of the tungsten 10% W/TiO$_2$: 10% tungsten on a titanium dioxide support 10% W/Al$_2$O$_3$: 10% tungsten on an alumina support 10% W/SiO$_2$: 10% tungsten on a silicon dioxide support 3.5% W/ZrO$_2$—Al$_2$O$_3$: 3.5% tungsten on a mixed support of 10% zirconium oxide and 90% alumina

DISCUSSION OF THE DATA

The data in Table I shows that the process of the invention (Samples 1–3) has a desirable combination of high activity and high selectivity. It also shows that unactivated zirconia (Sample 5) has excellent selectivity, but at a cost of such low activity that it can not be considered commercially useful. Sulfated zirconia (Sample 4) has good conversion and selectivity, but a high bromine number. The data also show that tungsten on other common catalyst supports (Samples 6–9) results in either low conversion, low selectivity, and/or a high bromine number. Several other catalysts (Samples 10–17) are shown for general comparative purposes.

When compared to current commercial SPA catalysts, the catalysts of the invention have significantly lower bromine number at 100% conversion with similar selectivity. The zeolite catalysts tested showed a wide range of activity. The LZY-82 and mordenite catalysts, although exhibiting excellent activity, produced significantly increased polyalkylated species, and therefore, decreased selectivity.

TABLE I

| Sample | Catalyst Description | % Conversion C$_3$ | % Conversion C$_6$ | % Selectivity C$_3$ | % Selectivity C$_6$ | % Di + Tri Alkylated | Bromine Number |
|---|---|---|---|---|---|---|---|
| 1 | 15% W/ZrO$_2$ | 100 | 7.91 | 97.2 | 98.5 | 0.221 | 0 |
| 2 | 15% W/ZrO$_2$ | 100 | 8.69 | 95.2 | 97.5 | 0.399 | 3 |
| 3 | 3.5% W/ZrO$_2$ | 100 | 7.05 | 94.4 | 97.1 | 0.389 | 4 |
| 4* | Sulfated ZrO$_2$ | 100 | 7.69 | 94.4 | 97.6 | 0.366 | 43 |
| 5* | Unactivated ZrO$_2$ | 6.2 | 0.22 | 100 | 100 | — | N/A |
| 6* | 10% W/Al$_2$O$_3$ | 100 | 6.37 | 80.3 | 87.2 | 1.195 | 57 |
| 7* | 3.5% W/ZrO$_2$-Al$_2$O$_3$ | 94.9 | 6.17 | 85.7 | 93.0 | .839 | 585 |
| 8* | 10% W/SiO$_2$ | 0 | 0 | — | — | 0 | N/A |
| 9* | 10% W/TiO$_2$ | 0.3 | 0.2 | — | — | 0 | N/A |
| 10* | SPA-M | 98.2 | 7.76 | 98.2 | 99.3 | 0.078 | 170 |
| 11* | SPA-U | 100 | 6.92 | 93.4 | 98.0 | 0.27 | 130 |
| 12* | LZY-82 | 100 | 7.37 | 93.5 | 97 | 0.458 | 13 |
| 13* | H + — Mordenite | 100 | N/A | 83.8 | 91.3 | 1.242 | 15 |
| 14* | H + — Y | 97.5 | N/A | 83.8 | 91.3 | 1.242 | 15 |
| 15* | H + — X | 0 | — | — | — | — | N/A |
| 16* | H + — L | 0 | — | 0 | 0 | 0 | N/A |
| 17* | SP-115 | 0 | — | — | — | 0 | N/A |

\* = Not an example of the invention.

What is claimed is:

1. A method of alkylating an aromatic compound with an alkene, comprising contacting the aromatic compound and the alkene together in the presence of an oxide of zirconium which has been activated with an acidic tungsten moiety, under effective alkylation conditions.

2. The method of claim 1 wherein the oxide of zirconium is zirconium oxide.

3. The method of claim 2 wherein the zirconium oxide is in the orthorhombic form.

4. The method of claim 2 wherein the zirconium oxide is in the monoclinic form.

5. The method of claim 1 wherein said oxide of zirconium which has been activated with an acidic tungsten moiety has been activated with the aid of calcination.

6. The method of claim 5 wherein the tungsten is in the form of ammonium meta tungstate before calcination.

7. The method of claim 1 wherein the aromatic compound is benzene, toluene, xylene, phenol, furan, a cresol, resorcinol, a phenyl ether, a phenone, or a sulfur-containing analog thereof.

8. The method of claim 7 wherein the aromatic compound is benzene, toluene, or xylene.

9. The method of claim 1 wherein the alkene has one olefinic bond.

10. The method of claim 9 wherein the olefinic bond is an α-unsaturation.

11. The method of claim 9 wherein the alkene is unbranched.

12. The method of claim 11 wherein the alkene has 2 to 32 carbon atoms.

13. The method of claim 12, wherein the alkene has 2 to 18 carbon atoms.

14. The method of claim 13, wherein the alkene has 3 to 10 carbon atoms.

15. The method of claim 14 wherein the alkene comprises propylene.

16. The method of claim 1 wherein said contacting takes place at elevated temperature.

17. The method of claim 16 wherein the elevated temperature is 100° C. to 300° C.

18. The method of claim 17 wherein the elevated temperature is 100° C. to 250° C.

19. The method of claim 1 wherein said contacting takes place at elevated pressure.

20. The method of claim 19 wherein the elevated pressure is 50 to 7,000 kPa.

21. The method of claim 20 wherein the elevated pressure is 2,000 to 4,000 kPa.

22. The method of claim 1 wherein the zirconia is zirconium oxide in the orthorhombic or monoclinic form; the aromatic compound is benzene, toluene, or xylene; the alkene is propylene or α-butene; and the contacting takes place at 100° C. to 300° C. and a pressure of 2,000 to 4,000 kPa.

* * * * *